United States Patent
Koch

(10) Patent No.: US 6,716,219 B1
(45) Date of Patent: Apr. 6, 2004

(54) SURGICAL OPERATION SYSTEM

(76) Inventor: Hans-Reinhard Koch, Friedrich-Ebert-Strasse 23, D-53177 Bonn (DE)

( * ) Notice: Subject to any disclaimer, the term of this patent is extended or adjusted under 35 U.S.C. 154(b) by 0 days.

(21) Appl. No.: 09/700,771

(22) PCT Filed: May 19, 1999

(86) PCT No.: PCT/DE99/01499
§ 371 (c)(1),
(2), (4) Date: Feb. 9, 2001

(87) PCT Pub. No.: WO99/59510
PCT Pub. Date: Nov. 25, 1999

(30) Foreign Application Priority Data

May 20, 1998 (DE) .......................................... 198 22 734
Jun. 26, 1998 (DE) .......................................... 198 28 677

(51) Int. Cl.⁷ ................................................. A61F 9/007

(52) U.S. Cl. ................................. 606/107; 606/1; 606/4; 606/166; 604/22; 607/1; 422/300

(58) Field of Search ................................. 606/1, 4, 107, 606/166, 167; 604/19, 22; 607/1; 422/300

(56) References Cited

U.S. PATENT DOCUMENTS

| 5,249,121 A | 9/1993 | Baum et al. ........... 364/413.01 |
| 6,068,627 A * | 5/2000 | Orszulak et al. .............. 606/34 |
| 6,251,113 B1 * | 6/2001 | Appelbaum et al. ........ 606/107 |

FOREIGN PATENT DOCUMENTS

EP 0596314 5/1994

* cited by examiner

Primary Examiner—Robert J. Warden, Sr.
Assistant Examiner—Sean E. Conley
(74) Attorney, Agent, or Firm—Milde & Hoffberg, LLP

(57) ABSTRACT

The invention relates to an operation system for supporting microsurgery operations, e.g., operations through which the natural crystalline lens is replaced by an artificial intraocular lens. The operation system comprises several surgical instruments (5) which are inserted into a receptacle (5), where they are connected to a connection tube (21), e.g., lines for liquids (22, 23) and/or electrical lines (24). The receptacle (4) for a surgical instrument can be docked on a supply unit (2) on which several connections for the supply of the corresponding surgical instruments are provided at various connection points. A control unit (41) recognizes by means of a decoding connection (17) which surgical instrument (5) is connected in its receptacle to the supply unit.

15 Claims, 5 Drawing Sheets

SURGICAL OPERATION SYSTEM

BACKGROUND OF THE INVENTION

The invention concerns a surgical operation system, particularly an ophthalmologic surgical operation system for use during micro-surgical operations, particularly, ophthalmologic operation systems which utilize a supply unit providing at least one consumable, such as electric power, compressed air and/or a fluid, and multiple surgical instruments that are interchangeably connected to the supply unit using connecting tubes that carry the necessary consumables to the respective surgical instrument.

Over the past few years, the significance of micro-surgical operations in all surgical fields has increased considerably. A characteristic of such operations is the use of many different and various surgical instruments that often must be quickly interchanged.

An example is the removal of the natural optical lens of the eye because of clouding by cataract, and its replacement with an artificial intra-ocular lens. Ophthalmologic surgical operation systems (so-called phaco-machines) are used during such an operation. The phaco-machine includes a central supply unit with electrical power supply, a high-frequency generator, a tube and connecting system for surgical instruments, so-called head units, infusion bottles for rinsing fluid, and one or more pumps. If the head units are powered by compressed air, this is also provided.

Such a phaco-machine is known from the U.S. Pat. No. 5,249,121 wherein a central supply unit several head units is connected to. In this case, these include a piezo-electric-driven ultra-sound phaco-emulsification device, an aspiration and irrigation device, and a small light tube.

An ophthalmologic aspiration and irrigation system is known from European Patent No. 0 596 314 with which intra-ocular pressure during an operation may be held stable by introducing optionally a gaseous or fluid medium. The system includes a pressure unit, an aspiration unit, and an irrigation unit in the form of interchangeable inserts into a housing, which are connected together via external lines.

Head units are inserted into the interior of the eye through a small slit in the cornea. These head units are then used to penetrate the encapsulating sac containing the natural lens. Thereafter, the natural lens is shattered by ultra-sound from a phaco-emulsification device, the so-called phaco-head unit, and the fragments are vacuumed out using an aspiration and irrigation device and rinsing fluid. Other head units used include bi-polar high-frequency coagulators (to prevent hemorrhaging, or penetration of the encapsulating sac by the lens shards). The operator observes the operation area using an ophthalmologic stereomicroscope. He usually controls the head unit function by means of a foot switch.

When another head unit is required in the course of an operation, e.g., an aspiration and irrigation device instead of a phaco-head unit, the head unit formerly used must be disconnected from the supply tube and line connecting it to the phaco-machine, and the new head unit must be connected. Additionally, the supply unit must be re-adjusted in order to ensure proper supply to the new head unit. An adjustment unit such as a keypad, rotating switch or similar device is provided for this purpose so that the supply parameters may be adjusted for each operating device. Thus, for example, only one electrical connection is required for an electro-cauterizer, and no connection is required to an aspiration and irrigation device (thus, no fluid connections); such fluid connections are required, however, for the phaco-head unit and for a vitrectomy head unit.

Since such internal eye operations must be performed as quickly as possible in order to prevent unnecessary irritation to the patient and other side effects, the operator must have optimal support during the operation, particularly during exchange of head units so that the necessary new parameters for a head unit may be quickly and reliably set when the head unit is connected. This has usually been performed either by the operator himself or by a nurse participating in the operation and monitoring the proper function and manipulation of the phaco-machine. Therefore, optimal cooperation of the operating team is a requirement for rapid and successful machine operation.

A problem with existing phaco-machines is sterility and sterilization of the entire surgical operation system. If, for example, a head unit must be replaced because of improper sterilization, then the replacement of tubes with sterile ones, the filling of the tubes, the routing of the tubes through specified guides in the machine, and the establishment of connections between the pump and the pressure sensors (depending on the type of phaco-machine) can require from five to ten minutes for conventional phaco-machines. If it is necessary to re-configure the phaco-machine during the operation on a patient, this interval can be very long not only for the patient, but also for the operating team. Even sterilization of phaco-machine parts requires time. If, for example, a head unit must be sterilized, the head unit with its connecting tubes and lines must be disconnected from the phaco-machine and then sterilized in the sterilizer. Then a sterile head unit with its connecting tubes and lines must be connected to the phaco-machine, and the tubes must be filled with rinsing fluid. This reconfiguration is complicated and time-consuming.

Even the exchange between various head units is complicated for conventional phaco-machines. For this, both the hose and electrical connections of the used head unit must be disconnected and reconnected to the new head unit. Then the machine must be re-adjusted using the control unit so that the supply unit is informed regarding the necessary supply parameters for the new head unit. Only then can the operation continue with the new head unit. Repeated exchanges between various head units are very time-consuming and inconvenient with conventional systems, and can also cause additional risks if a new head unit is urgently needed, or when readjustment to the phaco-machine is required.

SUMMARY OF THE INVENTION

The principal objective of the present invention is to provide a conventional surgical operating system, particularly an ophthalmologic surgical operating system, so that any head unit required by the operator is quickly available to him, and such that re-adjustment of any necessary surgical operating system parameters is performed reliably. Additionally, reliable data should be displayed to the user that informs him/her regarding the functional condition of the operating system. It should particularly ensure that all units are in the condition and status required for the operation.

This object, as well as other objects which will become apparent from the discussion that follows, are achieved, according to the present invention, by providing a surgical operation system wherein the supply unit includes several connection interfaces, one for each surgical instrument; each surgical instrument is stored in its own sterilizer unit that is connectable to a connection interface; each sterilizer unit includes an identifying coded connector for the surgical instrument that fits into a querying connector of the supply unit when the sterilizer unit is connected to the supply unit; and a control unit is connected to all the connection interfaces using the querying connectors, it identifies the connected surgical instrument for each connection interface and it sets the parameters for its supply of consumables Accordingly, the surgical operating system, e.g., the above-mentioned phaco-machine, includes a supply unit with several connection interfaces for each surgical instrument. Using this system, each surgical instrument is stored in a sterilizing unit which can be docked on the supply unit. Each sterilizing unit contains the head unit connection tubes and a roll-up mechanism for the head unit connection tubes. Further, it includes a coded identifying "querying" connector for the included head unit that connects to a corresponding mating connection on the supply unit when the sterilization unit is docked. This querying connector is connected with the control unit that supervises the function of the surgical operating system and that identifies the head unit connected to that connection interface. It also automatically adjusts the operating system parameters for the function of that particular head unit.

Preferably the supply unit is separated into a basic unit and a distributor unit provided with connection interfaces for the sterilizing units and connectable to the basic unit. This distributor system contains a tube system to supply the head unit with fluid and, when necessary, compressed air. This design of a surgical operating system is applicable and advantageous in many fields of surgery, and particularly in micro-surgery, particularly for such operations in which several surgical instruments must be interchanged. The following will refer to an ophthalmologic surgical operating system, a so-called phaco-machine, without prejudice to other potential uses.

Using the surgical operating system as described by the invention, it is possible to operate quickly and cleanly and most importantly under sterile conditions. When a head unit is removed from the sterilizer, the attached connecting tubes and any necessary electrical connections are also removed. When a head unit is returned into the sterilizer, the connections are automatically rolled up by the roll-up mechanism, so that the connecting tubes no longer lie around on an instrument tray and become entangled with one another.

With use of such a surgical operating system, the operation is considerably easier for the whole operating team. Thus, to change to a new head unit, the operator needs only to place the current head unit into its sterilizer (connections are automatically rolled up) and then take the next head unit from its own sterilizer in order to continue the operation. The control unit is automatically informed via activation sensors in the sterilizers when a head unit is replaced into its sterilizer and when the new head unit is removed from its sterilizer as to which head unit is current, and it then automatically adjusts system parameters for the new head unit. Exchange between various head units is thus possible without complications. Inconvenient exchange of head units (as is the case with conventional surgical operating systems such as the above-mentioned phaco-machine) is no longer necessary.

Automatic recognition of the latest head unit attached by means of coded connectors further excludes the risk that the head unit is exchanged but the operator forgets to re-adjust the operating system.

Overall, the operator enjoys extensive freedom in selection of available head units without suffering the risk of an improper system adjustment.

Thus, one has the option with a phaco-machine, for example, to dock two phaco-head units with different phaco-needles in separate sterilizers. The operator can thereby compare the effectiveness of different phaco-needles on one patient and select the most favorable one. It is also sometimes worthwhile to use two different phaco-needles or head units for two different purposes during one operation. Such options practically do not exist with conventional phaco-machines, since reconfiguration with another head unit as described above is possible only with significant loss of time, and such a method is normally not used.

A significant advantage of the invention with respect to conventional surgical operating systems is that the individual sterilizer units, or the sterilizer and the distributor unit, can easily be removed from the basic unit for purposes of cleaning, sterilization, or repair. Then another sterilizer or another distributor unit is docked with the basic unit. Work with the operating system may be continued without interruption. The operating system "down time" required with conventional systems for cleaning, sterilization, or repair is thus considerably reduced. Rapid interchangeability of a head unit with its supply lines in its own sterilizer also reduces the former risk of working with equipment that is not properly sterilized.

In order to clean the removed sterilizer or distributor unit, it is advantageous to provide a separate rinsing station to which the sterilizer or distributor unit may be docked according to the same principle, i.e., so that the rinsing station includes connection interfaces for distributor units and for sterilizers. As soon as a sterilizer or distributor unit is connected to the rinsing station, the tube system from the sterilizer or distributor unit is cleansed with rinsing fluid. The rinsing station can be designed as an "intelligent" station, in other words a control unit that automatically performs the cleaning steps. This rinsing station may be connected with the surgical operating system control unit via a data link so that the control unit receives the identification data and the cleansing status of the cleansed unit. Such a communication to the phaco-machine control unit can also be accomplished after sterilization. The data can also be manually provided to the control unit. It is also possible for the sterilizer and distributor units to include an electronic data buffer in which the procedures and processes performed on the unit are stored. Upon docking of the unit with the surgical operating system, the data are delivered to the control unit, and accepted as necessary,. In this manner, the control unit recognizes whether the docked unit has been properly prepared for use. If, for example, a non-sterilized unit is connected by mistake, then the control unit may issue an alarm and corresponding display.

The operating system may also include a counter mechanism by means of which the quantity of usages of a part of the surgical operating system may be determined. This counter mechanism would preferably be coupled with a timer mechanism that measures the usage time of the component monitored by the counter mechanism.

Preferably individual surgical instruments, individual sterilizers, and the distributor units are equipped with the counter and/or timer mechanism. Of course, the supply unit can also be equipped with such monitoring equipment.

Equipping the supply unit with such monitoring equipment specifically allows for the monitoring of the individual components, and allows for the issuance of a warning signal or limitation (or even shutdown) of a function in case usage limits established from experience are exceeded. This can thereby alert the user to maintain service intervals, for example.

The counter and/or timer mechanism used to monitor the sterilizer and surgical instruments or head units would preferably be mounted in the sterilizer so that the quantity of sterilizer and head unit usages can be registered. For the case of an ophthalmologic surgical operating system, the counter and/or timer mechanism could be so adjusted that, for example, after 50 usages of the surgical instrument (such as a phaco-head unit), the phaco-needle should be changed and the surgical instrument connecting tubes should be checked for integrity. After 100 cycles of the phaco-head unit in the sterilizer, an alert might be issued that the sterilizer and phaco-head unit should be returned to the manufacturer for service. If this does not occur, then, as mentioned above, function of the phaco-head unit can be blocked. In this manner, the user would to some extent be forced to perform (or have performed) prescribed servicing such as tube replacement, measurement of the head unit, and safety checks.

A counter mechanism also allows the number of cleanings, sterilization procedures, and servicings to be counted, and to be passed to the control unit. This can occur both for the sterilizer and for the distributor unit. Total counts from the counter and/or timer mechanism can be displayed at any time so that the user can have a visual image of the entire surgical operating systems readiness status.

A counter mechanism that records the number of cleanings, sterilizations, and servicings, etc., can be a simple mechanical or electronic unit that advances its count every time the sterilizer or distributor unit is docked to a servicing station. The quantity of counts can be displayed either on the sterilizer itself, the distribution unit or on a separate display via the control unit.

The counter mechanism can help ensure that, for example, the surgical instrument has been rinsed or sterilized properly after each use. This can be achieved via a corresponding display on the control unit. A function shut-down of the surgical operating component being monitored is also possible, and the shut-down would only be lifted when the component has been properly prepared for use, i.e., cleansed, rinsed, or sterilized.

Preferably, sterilizer sensors (such as small temperature sensors that determine whether the proper sterilizing temperature is achieved during a sterilization procedure) can be linked with the surgical operating components that must be sterilized at certain intervals. Preferably component function is restored by the control unit only after this is achieved.

Based on this invention the surgical operating system can be designed in modules so that the width of the sterilizer determines the width of the module. This modular design allows practically-any surgical operating system configuration so that it is possible to adapt the operating system to future developments. Thus, a new module can be connected to an existing basic unit that is suitable for connection to a newly-developed head unit with its sterilizer.

For a full understanding of the present invention, reference should now be made to the following detailed description of the preferred embodiments of the invention as illustrated in the accompanying drawings.

DESCRIPTION OF THE PREFERRED EMBODIMENT

Figure 1:
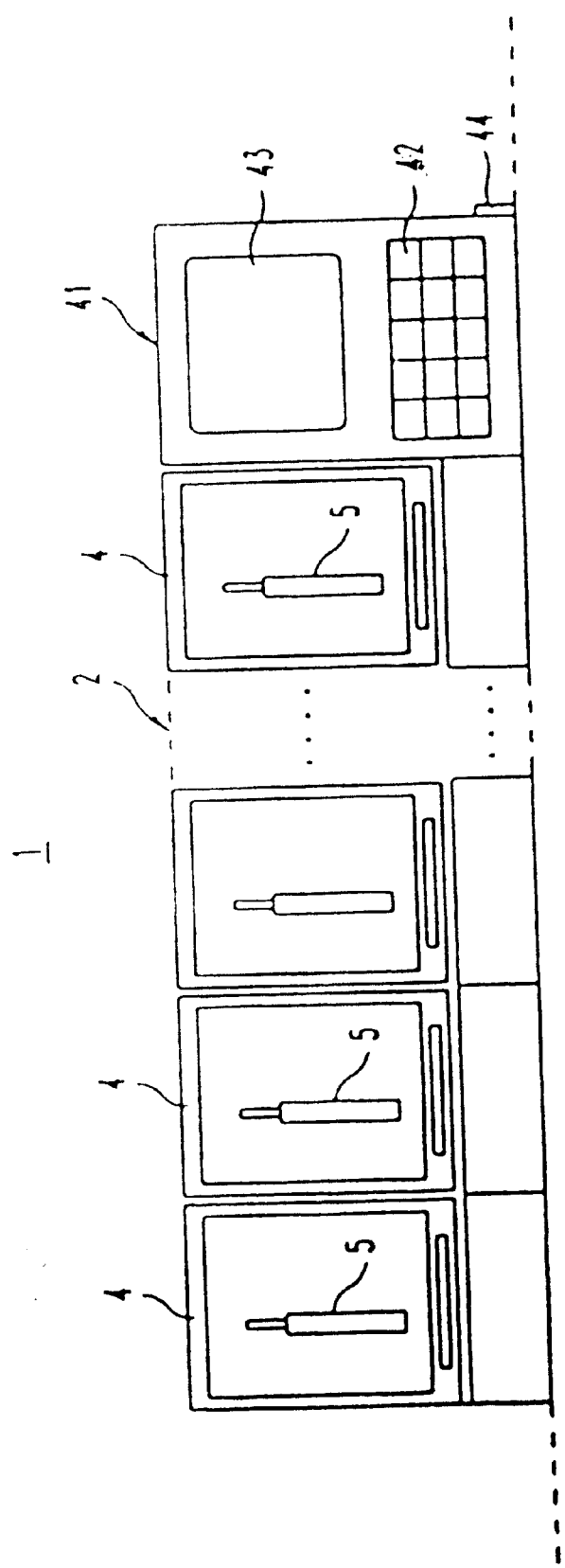
FIG. 1 a frontal view of a surgical operating system, namely a phaco-machine based on the invention that comprises a supply unit, a distributor unit, and several sterilizers, each for a head unit.

The preferred embodiments of the present invention will now be described with reference to FIGS. 1–5 of the drawings. Identical elements in the various figures are designated with the same reference numerals.

The figures show a phaco-machine 1 consisting of a basic unit 2, a distributor unit 3 that is dockable to it, and several sterilizers 4 (for head units 5) connectable to the distributor unit.

Each surgical instrument 5 includes a connecting tube 6 that is kept rolled up on a roller 7 within the sterilizer 4. This roller is preferably motor-driven. Depending on the type of the surgical instrument, the connecting tubes include fluid lines 8 and 9 as well as electrical lines 10. In this case, a phaco-head unit with two fluid lines and an electrical line is shown. The electrical connection may in turn contain additional lines, such as lines for operating current and data transmission, for example. These lines lead to a connecting plug 10 that engages a corresponding socket 11 when the sterilizer 4 is docked. At least some of the data lines lead to a coded connector 12 in the sterilizer that fits into a corresponding querying connector 13 in the basic unit 2 when the sterilizer 4 is docked. Connections 12 and 13 may form parts of the plug 10 or 11. The two fluid lines 8 and 9 lead to a connection 14 in sterilizer 4 that fit into a corresponding connection 15 in the distributor unit when the sterilizer 4 is docked. Connections 10 through 15 form a connection interface for a sterilizer 4 or a head unit 5.

Figure 3:
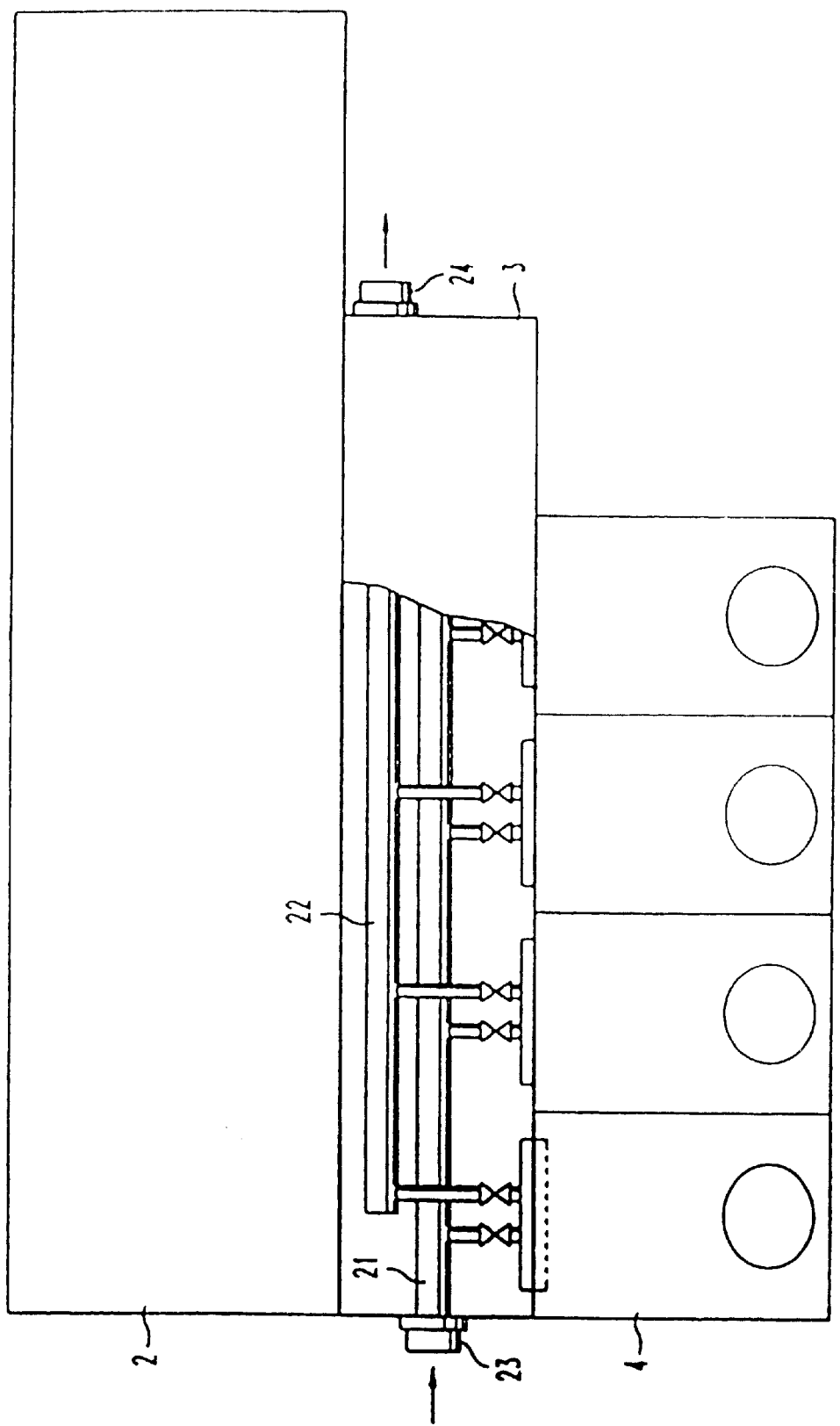
FIG. 3 a partial cutaway overhead view of the phaco-machine.
Figure 4:
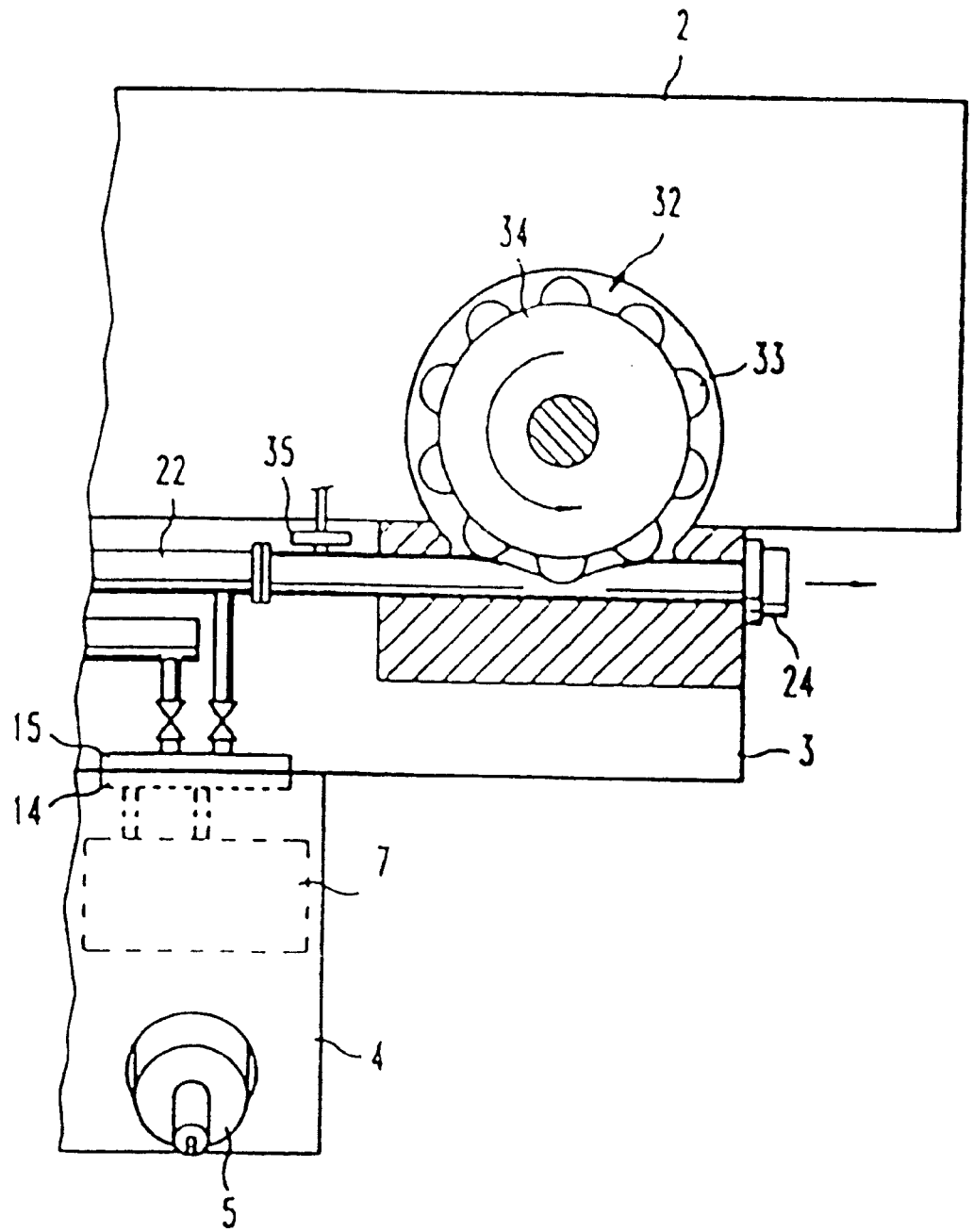
FIG. 4 a cutaway partial view of the phaco-machine in the area of a fluid pump.

As may be seen in detail in FIGS. 3 and 4, the distributor unit 3 is equipped with an internal line or tubing system consisting of an irrigation line, i.e., a pressure line 21, and an aspiration or vacuum line 22, whereby the pressure line 21 at one end of the distributor unit 3 is equipped with a connector 23, and the vacuum line 22 at the other end of distributor unit 3 is equipped with another connector 24. A cross-connector 25 branches from the pressure line 21 at each connection interface and contains an electrically-operated valve 26. It feeds into the connector 15 of the distributor unit 3. A similar cross-connector 27 also branches from the vacuum line 22 at each connector, cross-connector 27 also contains an electrically-operated valve 28, and it also feeds into the connector 15 at each connector. The lines are thus so arranged that when a sterilizer 4 is connected, the connector tube 8 is connected with the cross-connector 25, and connector tube 9 is connected with the cross-connector 27. A tube 29 is connected with connector 23 at the entrance to pressure line 21. Tube 29 leads to an infusion bottle 30 that hangs from a height-adjustable rack 31.

A pump 32 is provided for the vacuum line 22. This pump is preferably a tube pump, as is shown in FIG. 4. The tube pump 32 is mounted in the basic unit 2, extends through an opening in the distributor unit 3 into it, and operates with roller elements 33 on the circumference of a wheel 34 on the vacuum line 22 that is in the form of a flexible tube at least in this area, so that the rinsing fluid in it is transported from the infusion bottle 30. The connector 24 is connected with a drain. A pressure sensor 35 can be connected to the vacuum line 22 (see FIG. 4).

Figure 2:
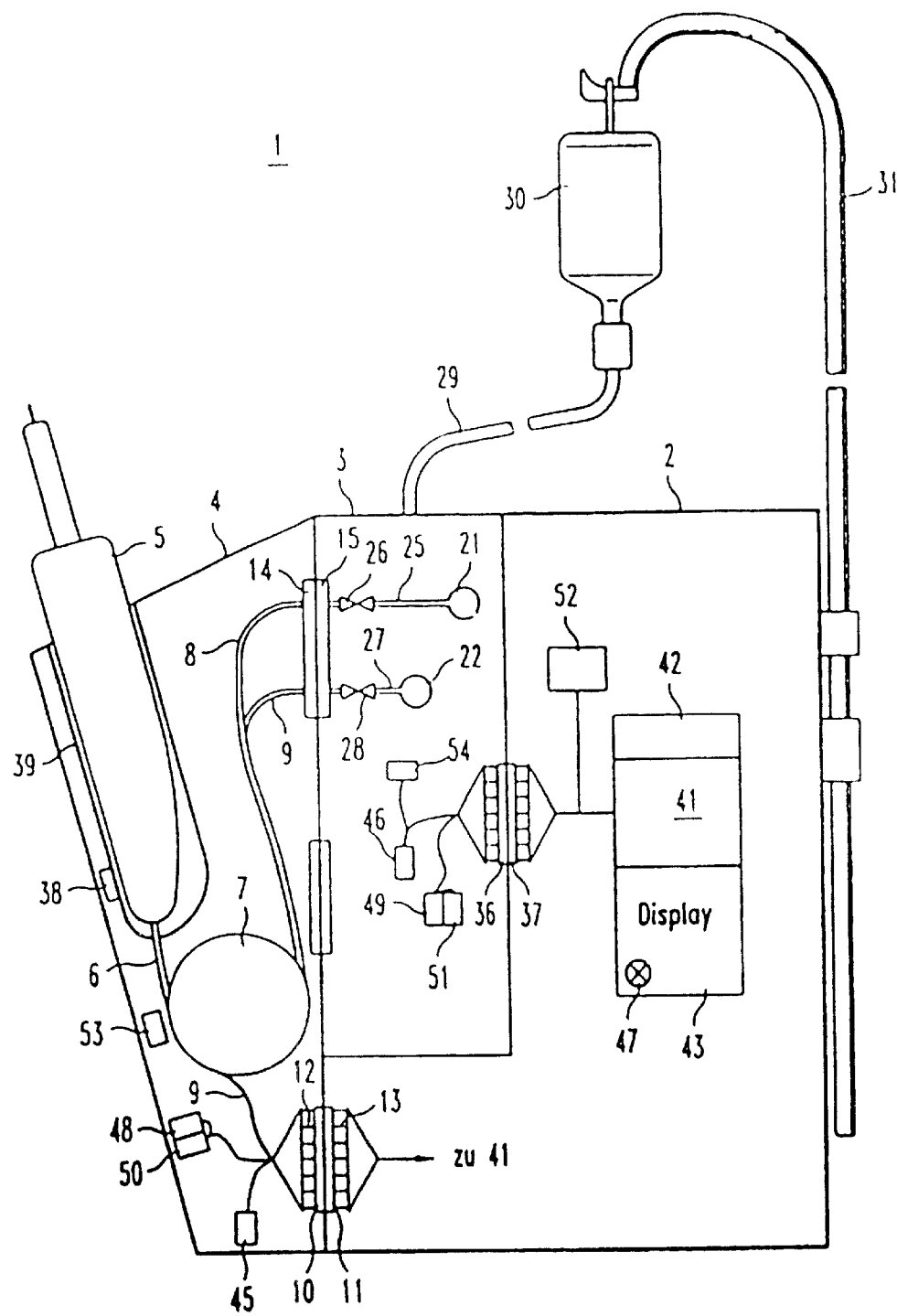
FIG. 2 a partial cutaway side view of the phaco-machine as shown in FIG. 1.

As is shown in FIG. 2, the distribution unit 3 is equipped with an electrical connector 36 that fits into a corresponding connector 37 of the basic unit 2 when the distributor unit 3 is docked with the basic unit 2. These connections provide, for example, operating power to valves 26 and 28. Additionally, data lines may be provided that report the status of valves 26 and 28, the fill status in lines 21 and 22, or the output signal of sensor 35, among other things.

In the phaco-machine described, additional sensors are provided as necessary that monitor the status of the phaco-machine. Examples might be activity sensors 38 that are located in a receptor depression 39 for a head unit 5 and that show whether the head unit 5 is located in the sterilizer 4 or has been removed from it.

Further, the height-adjustable rack 31 for the infusion bottle 30 may be equipped with a sensor 40 (only indicated in the figure) that shows the height of the infusion bottle 30 and thereby the pressure in the irrigation line 21. The height of the rack 31 may be adjusted either manually or, as not shown here, by a motor.

All signals from individual sensors and the code signals generated from connectors 12 and 13 are transmitted to a central control unit 41 that is a component of the basic unit 2, and, as shown in FIG. 1, can be connected to the basic unit 2 as a module. Based on the transmitted signals, the control unit 41 adjusts the parameters of the phaco-machine automatically. Supply for a head unit 5 is activated as soon as it is removed from its sterilizer 4. This includes the provision of fluid from the infusion bottle 30, the height setting of the infusion bottle 30, the settings for the valves 26 and 28 for the rinsing fluid, the setting of operating current for the head unit, the monitoring of pressure in the aspiration line 22, the action of the tube pump 32, etc. Head unit function can then be controlled by the operator by the above-mentioned foot switch, for example, without having to make any other adjustments to the phaco-machine. Signals from the foot switch are preferably transmitted using a wireless data link, e.g., radio-frequency, infrared, or ultrasonic, thus conventional cables which may lay on the floor can be avoided.

An input device 42 such as a keypad is connected to the control unit 41. Also, a display is provided, e.g., a monitor 43, which would show phaco-machine system parameters. The display can also include an optical or audible warning signal 47. Input devices other than a keypad 42 may be used, such as contact elements directly on the monitor. In addition to the monitor, other peripheral devices such as a printer may be connected via corresponding interfaces 44 that would produce a record of each operation.

The sterilizer 4 and the distributor unit 3 can also contain small electronic buffers 45 or 46 that are connected to data connections 10 or 36. Data regarding procedures such as cleansing, sterilization, etc. performed on the sterilizers and the distributor unit may be stored in these buffers. These data would then be passed to the control unit upon docking of a sterilizer or distribution unit so that functionality of the concerned unit might be checked.

In particular, the sterilizer and the distribution can each be provided with a counting mechanism 40 or 49 that is in turn coupled with a time counter 50 or 51. These would in turn be connected to data connections 10 or 36. A connection to the buffers 45 or 46 can also be provided. The basic unit 2 can include a monitoring unit, preferably a time counter 52.

These additional devices 48 through 52 pass their data regarding the number of usages of individual components such as the head units, the sterilizers, the distributor unit, and the basic unit to the central control unit 41, which in turn passes information to the user regarding any necessary servicing via the display 43 or the warning signal 47.

Temperature sensors 53 and 54 can also be included in the sterilizer 4 and the distributor unit 3 that determine the temperature of these components during sterilization and pass the information to the control unit 41 when these components are docked to the basic unit 2.

Figure 5:
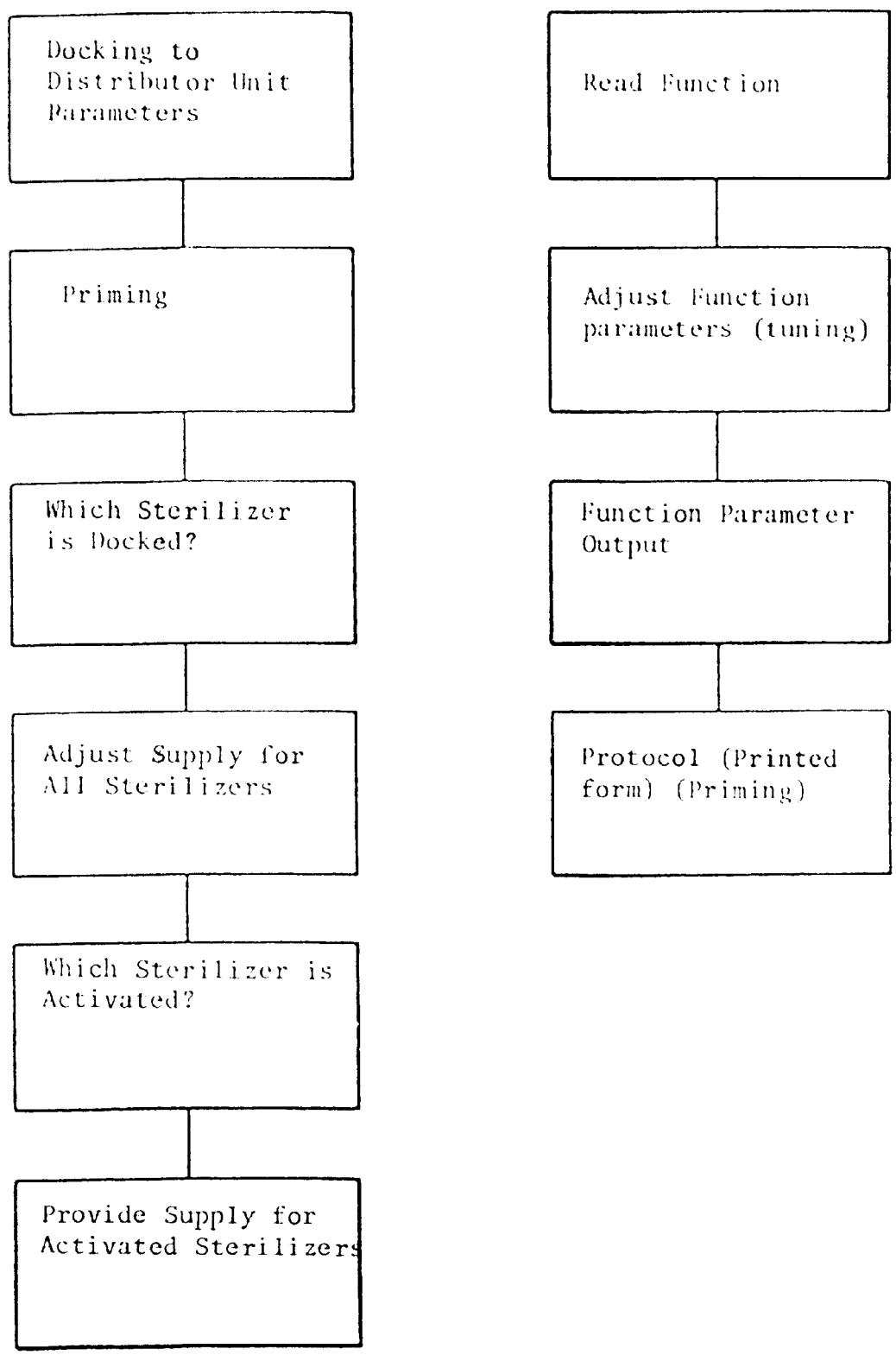
FIG. 5 a flow chart for a control unit of the phaco-machine based on the invention.

FIG. 5 shows a function chart for the phaco-machine described. When the distributor unit is docked with the basic unit the phaco-machine is prepared for an operation by filling the entire distributor unit tubing system with rinsing fluid. When a sterilizer is connected, the control unit receives a report from the coded connectors regarding which sterilizers have been docked, i.e., specific data for each head unit is transmitted to the control unit. Based on this information, supply for all sterilizers or head units is adjusted, the supply tubes in the distributor unit are filled with rinsing fluid, and any necessary electrical lines receive power and any necessary air lines receive compressed air. These preparatory procedures are known as "priming." Then, as soon as a head unit is extracted from a sterilizer, supply for this connection interface and the corresponding head unit is available. The operator then controls head unit function by means of the foot switch (not shown).

In parallel to these procedures, the phaco-machine function parameters are monitored continuously. These function parameters can be optimized by the operator, which is known as "tuning." A head unit used to shatter the natural lens of the eye operates, for example, at a nominal frequency of 40 kHz. In order to determine the optimum frequency and amplitude, the phaco-head unit is first placed into a testing vessel and optimized. This value is stored in the control unit. During the operation, however, the optimum frequency changes when the phaco-head unit comes into contact with the natural lens, so that a certain improvement or re-tuning is required. This re-tuning is performed either by the operator or automatically via a control unit test program.

Phaco-machine function parameters and the record of each operation may be displayed or printed as desired.

As shown in FIG. 1, the basic unit and, if necessary, the distributor unit, can be of modular design so that the width of each module is determined by the width of the sterilizer.

The previous discussion described a phaco-machine that includes only connections for the rinsing fluid and electrical connections for operating current or data transfer. Naturally it is possible to apply the principle of such a phaco-machine with sterilizers to air-driven head units. It is of course possible and conceivable to operate such a phaco-machine with other types of head units, e.g., with head units that use a laser beam to shatter the clouded natural lens of the eye.

Additionally, the preceding discussion describes the coding and querying connectors as electrical in nature. It is possible to use any other type of coding as long as it ensures that the control unit is informed regarding the type of the surgical instrument connected. Thus, for example, purely mechanical coding can be used. Of course, a combination of electrical and some mechanical coding mechanisms is possible.

There has thus been shown and described a novel surgical operation system which fulfills all the objects and advantage sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. In an operation system for use during micro-surgical operations, particularly ophthalmologic operation systems, comprising (a) a supply unit providing at least one consumable selected from the group consisting of electrical power, compressed air and a fluid; (b) multiple surgical instruments that are interchangeably connectable to the supply unit using connecting tubes that carry the necessary consumables to the respective surgical instrument; and (c) a control unit by means of which parameters regarding the supply of consumables to the surgical instruments is adjustable, the improvement wherein:

the supply unit includes several connection, interfaces, one for each surgical instrument;

each surgical instrument is stored in its own sterilizer unit that is connectable to a connection interface;

each sterilizer unit includes an identifying coded connector for the surgical instrument that fits into a querying connector of the supply unit when the sterilizer unit is connected to the supply unit;

the control unit is connected using the querying connectors to all connection interfaces, it identifies the connected surgical instrument for each connection interface, and it sets the parameters for its supply of consumables.

2. Operating system according to claim 1 wherein each sterilizer unit includes the necessary connection tubes for the surgical instrument contained therein, and a roll-up mechanism for the tubes.

3. Operating system according to claim 1 wherein the supply unit is divided into a basic unit and a separate distributor unit equipped with connection interfaces for the sterilizer units and connectable to the basic unit, where the distributor unit accepts a tube system connected with a supply and an exhaust at each connection interface to supply the surgical instruments with at least one of a rinsing fluid, and compressed air.

4. Operating system according to claim 1, further comprising activation sensors that pass an activation signal to the control unit (41) when any surgical instrument (5) is withdrawn from its sterilizer unit, the activation signal causing the control unit to activate the supply for the surgical instrument.

5. Operating system according to claim 1, wherein the control unit includes an input device to program the operating system functions.

6. Operating system according to claim 4, wherein the control unit includes a display that shows an operating system function.

7. Operating system according to claim 1, wherein the control unit is provided with an interface for connection of external devices, particularly a printer.

8. Operating system according to claim 1, wherein the sterilizer unit and the distributor unit are each provided with a buffer in which specific data from the sterilizer unit and the distributor unit may be entered, and that the data can be transferred to the control unit when docked with the basic unit.

9. Operating system according to claim 1, wherein the operating system includes a counter mechanism used to count the number of usages of at least a component of the operating system.

10. Operating system according to claim 1, wherein the operating system includes a timer mechanism used to measure the usage time of at least a component of the operating system.

11. Operating system according to claim 9, wherein the counter mechanism and/or the timer mechanism is connected with the central control unit.

12. Operating system according to claim 9, further comprising a display for the count and/or duration of usages of at least one of the components monitored by the counter and/or timer mechanism.

13. Operating system according to claim 9, the control unit issues a signal, especially a warning signal, when a predetermined number of usages and/or a predetermined amount of usage time is exceeded for at least one part of the operating system.

14. Operating system according to claim 9, wherein the function of at least one of the operating system components monitored by the counter and/or timer mechanism has its function limited or blocked when a predetermined number of usages and/or a predetermined amount of usage time is exceeded.

15. Operating system according to claim 1, wherein temperature sensors are provided for operating system parts to be sterilized.

* * * * *